United States Patent [19]

Tice et al.

[11] Patent Number: 4,585,482
[45] Date of Patent: Apr. 29, 1986

[54] LONG-ACTING BIOCIDAL COMPOSITIONS AND METHOD THEREFOR

[75] Inventors: Thomas R. Tice, Birmingham; William E. Meyers, Helena; Richard M. Gilley, Birmingham; William M. Shannon, Birmingham, all of Ala.

[73] Assignee: Southern Research Institute, Birmingham, Ala.

[21] Appl. No.: 614,231

[22] Filed: May 25, 1984

[51] Int. Cl.[4] ............................................. C09D 5/14
[52] U.S. Cl. ........................ 106/15.05; 252/187.21; 252/187.23; 424/149
[58] Field of Search ............... 252/187.21, 187.23; 424/149; 106/15.05

[56] References Cited

U.S. PATENT DOCUMENTS

| | | | |
|---|---|---|---|
| 2,482,891 | 9/1949 | Aston | 252/187.23 |
| 3,885,910 | 5/1975 | Fischer et al. | 252/187.23 |
| 4,084,747 | 4/1978 | Alliger | 252/187.23 |
| 4,310,425 | 1/1982 | Key et al. | 252/187.21 |

Primary Examiner—Lorenzo B. Hayes
Attorney, Agent, or Firm—Hopgood, Calimafde, Kalil, Blaustein & Judlowe

[57] ABSTRACT

There is disclosed, in one aspect, a long-acting biocidal composition. This composition comprises a chlorine dioxide-liberating compound, such as sodium chlorite, and sufficient organic acid-generating compound, such as poly(lactic acid), to lower the pH of the composition to less than about 7. The organic acid-generating compound is present in a form whereby it is released gradually in the presence of water. Preferably the organic acid-generating compound is encapsulated within or by a film-forming polymer. In another aspect, there is disclosed a method of disinfecting a surface over a prolonged period of time. This method comprises applying to the surface a small but effective amount of the long-acting biocidal composition described above.

16 Claims, 2 Drawing Figures

LONG-ACTING BIOCIDAL COMPOSITIONS AND METHOD THEREFOR

BACKGROUND OF THE INVENTION

This invention relates generally to biocidal compositions and methods for using these compositions. In particular, this invention relates to long-acting biocidal compositions which may remain effective for weeks, months or even years.

The use of various disinfecting and sterilizing compounds to disinfect surfaces is known in the art. Chlorine compounds have been used for this purpose. Chlorine dioxide, in particular, has been found to be an especially effective germ killer. This compound is quite versatile and has been used as a bleaching agent such as in the oxidation of the natural colorant present in cotton, wood pulp, and other cellulosic fibrous materials. In these uses, the chlorine dioxide oxidizes the treated material yet is noninjurious to the fibrous materials.

Chlorine dioxide has also been used in the treatment of water supplies. It is commercially available in powder form for use in swimming pools, and in liquid form for use in household and industrial cleaning and disinfecting.

Chlorine dioxide is generally considered to be at least as effective as, if not superior to, chlorine gas as a bactericide, sporicide or virucide. Moreover, chlorine dioxide retains its germ-killing capacity to a significantly greater extent over a wider pH range than does gaseous chlorine.

Due to its explosive nature in concentrated form, chlorine dioxide gas is not generally used directly as a chemical reagent. It has instead become the general practice to use a chlorine dioxide-liberating compound such as sodium chlorite as the source of the chlorine dioxide gas.

Sodium chlorite has been found to form a particularly effective germ-killing composition when combined with lactic acid. U.S. Pat. No. 4,084,747 discloses germ-killing compositions and methods which employ sodium chlorite and lactic acid in aqueous solution. U.S. Pat. No. 4,330,531 discloses various germ-killing materials such as gels, toothpastes and soaps which are prepared using sodium chlorite and lactic acid as the active germ-killing ingredients.

Although prior art uses of compositions which employ a chlorine dioxide-liberating compound and a weak organic acid, such as lactic acid, have been successful as disinfectants, the germ-killing action has not been maintained for very long beyond the time of application. For this reason, surfaces which have been successfully disinfected may be susceptible to recontamination within a fairly short time.

The reaction of a chlorine dioxide-liberating compound, such as sodium chlorite, and lactic acid is completed within a relatively short period of time and the chlorine dioxide diffuses after it is released. Accordingly, the chlorine dioxide dissipates rather quickly from the microenvironment which exists immediately above the treated surface. This leaves the recently treated surface unprotected against recontamination.

The search has continued for long-acting disinfectant and biocidal compositions, and methods of making and using such compositions. This invention was made as a result of that search.

OBJECTS AND SUMMARY OF THE INVENTION

Accordingly, it is a general object of the present invention to avoid or substantially alleviate the above-discussed problems of the prior art.

A more specific object of the invention is to provide biocidal compositions which will remain effective over an extended period of time.

Another object of the invention is to provide biocidal compositions which are also non-toxic and may be applied to work surfaces and clothing.

A further object of the invention is to provide biodical compositions which may be made to adhere to the surfaces which are to be treated.

Yet another object of the present invention is to provide a method of making these biodical compositions.

An additional object of the invention is to provide a method of disinfecting a surface over a prolonged period of time.

Still other objects and advantages of the present invention will become apparent from the following summary of the invention and description of its preferred embodiments.

The present invention provides, in one aspect, a longacting biocidal composition. This composition comprises a chlorine dioxide-liberating compound and sufficient organic acid-generating compound to lower the pH of the composition to less than about 7. The organic acid-generating compound is present in a form whereby it is released gradually in the presence of water.

In another aspect, the present invention provides a method of disinfecting a surface over a prolonged period of time. This method comprises applying to the surface a small but effective amount of the biocidal composition described above.

DETAILED DESCRIPTION OF THE PREFERRED EMBODIMENTS

Figure 1:
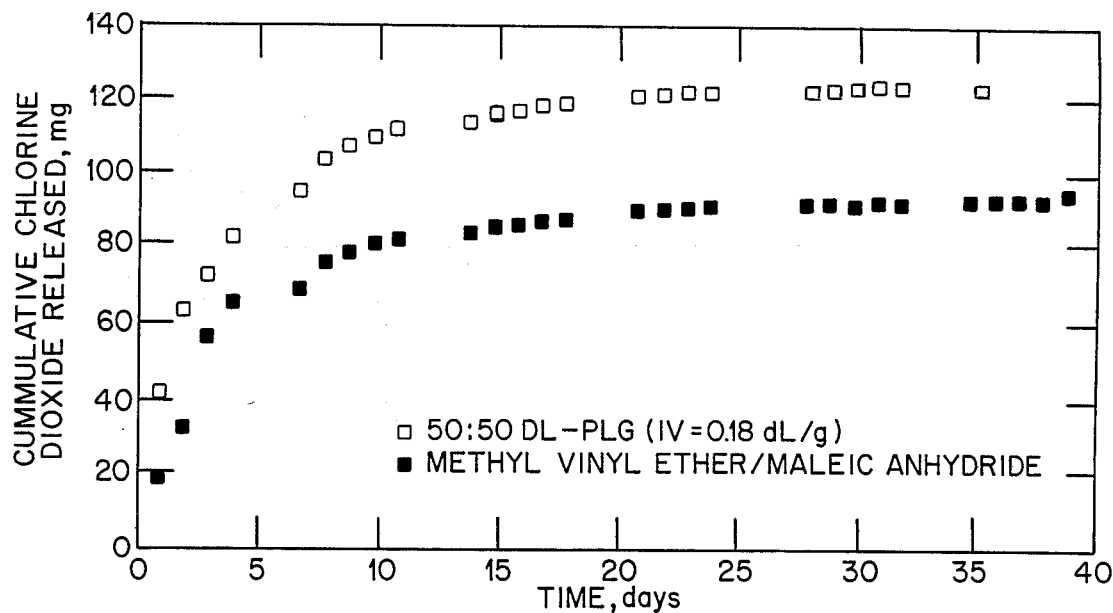
FIG. 1 is a graph showing the release of chlorine dioxide over time from compositions containing sodium chlorite and either methyl vinyl ether/maleic anhydride or low-molecular-weight 50:50 DL-PLG copolymers.

The long-acting biocidal composition of the present invention employs a chlorine dioxide-liberating compound as one of the components of the disinfectant composition. By "chlorine dioxide-liberating compound" is meant any compound which when appropriately treated will liberate chlorine dioxide. While any chlorine dioxide-liberating compound may be used, water-soluble chlorites are preferred because they are readily available and inexpensive. Typical water-soluble chlorites include alkali metal chlorites and alkaline earth metal chlorites. Sodium chlorite and potassium chlorite are preferred. Sodium chlorite is particularly preferred.

Mixtures of two or more chlorine dioxide-liberating compounds may also be used.

The biodical composition also employs an organic acid-generating compound in a form whereby organic acid is gradually generated in the presence of water. In a preferred embodiment, the organic acid generating compound is in the form of a gradually hydrolyzable polymer.

The term "organic acid-generating compound" as used in this specification includes carboxylic acids, esters, anhydrides, and acyl halides. Furthermore, these may be used in either monomeric, oligomeric or polymeric form. It is generally preferred that the organic acid-generating compound exhibits low water solubility as the unhydrolyzed starting material, but increased water solubility after the generation of the acid.

In addition to the esters, anhydrides, and acyl halides discussed above, the corresponding derivatives employing phosphorous, sulfur, and boron are similarly useful.

Typical polyesters include the homopolymers polylactic acid, polyglycolic acid, polyhydroxy butyrate, and polycaprolactone, copolymers thereof, or a physical mixture of homopolymers and/or copolymers, wherein the ester linkage forms the backbone of the polymer, or polymers with pendant ester groups such as polymethylmethacrylate, polyvinyl acetate, the polyoxalates, polydioxanone, the polyortho esters, polyphosphonate esters, polyboronate esters, and polysulfonate esters. Typical monomeric esters include esters prepared from carbonyl acids having generally one to twenty, and typically two to ten carbon atoms in their chain and alcohols having a similar number of carbon atoms in their chain. The carbonate, phosphate, and sulfonate diesters may also be used.

Typical anhydrides include maleic anhydride, succinic anhydride, and their perfluorinated equivalents which demonstrate substantial increase in solubility with hydrolysis. These compounds generate two acid groups with each hydrolysis step. Mixed straight-chain anhydrides are also useful. Polyphosphate anhydrides, such as adenosine triphosphate and pyrophosphate are also useful.

Two types of polymeric anhydrides may be used. The first type includes those in which the anhydride is contained within the backbone of the polymer. The second type includes those in which the anhydride group is pendant to the backbone, such as the GANTREZ polymers.

Anhydrides formed from polymers having pendant acid groups, such as polyacrylic acid, and any other carbonyl acid may also be useful.

For both esters and anhydrides, the incorporation of electron withdrawing and donating groups in either the acid portion or, in the case of the esters, the alcohol portion, may be used to control the rate of hydrolysis and thus acid production.

Acyl halides and the phosphorous and sulfonyl analogs thereof (such as benzoyl chloride and tosyl chloride) and polymeric analogs (such as polyacryloyl chloride) where the halide may be selected from among chloride, bromine, and fluorine, may also be used.

A catalyst may also be used to control the rate of acid production by enhancing the rate of hydrolysis of compounds such as those listed above. These catalysts may be simple organic or inorganic compounds, such as imidiozole or phosphate, or they may be complex species of biological origin such as the proteolytic enzymes and esterases, the lipases responsible for the hydrolysis of fatty acid esters, the phosphatases, such as alkaline phosphatase, which are responsible for the hydrolysis of phosphate esters, or combinations of enzymes such as amylase or the cellulase enzymes capable of converting polysaccharides to glucose coupled with glucose oxidase enzyme which then rapidly converts glucose to an acidic derivative.

Acids of low water solubility may also be used. The rate of solvation of these acids determines the rate at which acid is generated. The greater the hydrophobicity of the acid, the slower the rate of solvation.

For all of the organic acid-generating compounds mentioned above, the physical form of the organic acid generating compound is important to its rate of action. For example, fine particulate dispersions of the organic acid generating compound generate acid more rapidly than large chunks or beads of the organic acid-generating compound.

The preferred organic acid-generating compounds of this invention are such that when reacted with a chlorine dioxide-liberating compound, they generate lactic, citric, malic, tartaric, glycolic, mandelic or other structually similar acids.

Mixtures of two or more organic acid-generating compounds may also be used.

The pK of these generated organic acids may be generally from about 2.8 to about 4.2, and preferably from about 3.0 to about 4.0.

The rate of acid generation may be varied by regulating the molecular weight of the organic acid-generating polymer employed. For example, the use of a larger-molecular-weight polymer will produce a slower rate of acid generation. The rate of acid generation may also be varied by regulating the size of the particles of the organic acid-generating compound. For example, use of larger particles will produce a slower rate of acid generation.

In a preferred embodiment, a humectant is used in connection with the other components of the long-acting biocidal composition of this invention. A humectant is a substance which has affinity for water and effects a stabilizing action on the water content of the composition within a narrow range. The humectant is used in the compositions of the present invention to ensure the presence of a certain amount of water.

The humectants used in this invention are well known to those skilled in this art and typically include vicinal polyhydroxy compounds, and preferably vicinal dihydroxy compounds. Examples of humectants suitable for use in this invention include glycerol and sorbitol.

The amount of chlorine dioxide-liberating compound that may be used in this composition may be generally from about 0.01 to about 1, typically from about 0.02 to about 0.5, and preferably from about 0.03 to about 0.3% by weight of the total composition.

The amount of organic acid-generating compound that may be used should be sufficient to lower the pH of the composition to less than about 7, typically from about 2 to about 5, and preferably from about 2.2 to about 2.7. Furthermore, this amount should be such that the amount of organic acid generated is generally from about 0.01 to about 6, typically from about 0.05 to about 3, and preferably from about 0.1 to about 2% by weight of the total composition.

The amount of humectant may vary widely but in the present invention there is employed generally less than about 50, typically from about 1 to about 20, and preferably from about 2 to about 10 percent by weight of the total composition.

The long-acting biocidal compositions of this invention may be prepared in several forms. In one embodiment, solid organic acid generating compound and chlorine dioxide-liberating compound are merely admixed. For example, solid poly(lactic acid) (DL-PL) and solid sodium chlorite may be admixed and this composition may be used, for example, as a biocide in air conditioning systems. The solid admixture is stable until added to water when it reacts to form the biocidal agent.

In another embodiment, solid organic acid-generating compound may be encapsulated within a film forming polymer and the chlorine dioxide-liberating compound may be diffusion loaded into the microcapsules formed by the film forming polymer. The microcapsules are then coated with a hydrophobic polymer to retain the water and sodium chlorite. Using this method, there is produced hard, unagglomerated microcapsules having continuous polymer walls. These microcapsules exhibit a slow release of chlorine dioxide.

In another embodiment, the biodical composition is prepared by first forming microspheres of the organic acid-generating compound and encapsulating them as well as the chlorine dioxide-liberating compound within a film forming polymer. The process produces hard microcapsules that may be isolated by filtration.

In a preferred embodiment, the encapsulating film has contained within the film itself the organic acid-generating compound. In this preferred embodiment, there would be a release of organic acid within the microcapsule and the reaction of the acid with the chlorine dioxide-liberating compound. The film forming polymers which may be used to encapsulate the organic acid-generating compound may be any film-forming polymer which will permit chlorine dioxide to be released within the film as the acid is generated. Preferred film forming polymers include polyamides such as NYLON polyamides and thermoplastics such as polystyrene.

Since sufficient amounts of water must be provided and maintained within the capsules to allow the necessary hydrolysis and/or other reaction to take place, it may be necessary to provide the capsules with protection against loss of water in certain embodiments.

In one such embodiment, the encapsulating film may be further treated with a hydrophobic material to protect against water loss. Hydrophobic film-forming polymers may generally be useful in this embodiment. Polystyrene and ethyl cellulose are particularly preferred. This hydrophobic film may also be employed as a second, outer encapsulating layer.

The biocidal compositions of this invention may be used by applying them to any surface or substrate which one wishes to disinfect. The term "surface" as used in the instant specification is intended to cover any type of substrate or carrier which could provide a locus for the accumulation of germs, virus, spores, bacteria, fungi, i.e., all types of parasitic microorganisms. Obvious examples include surgical and dental instruments, food containers, human and animal skin, tissue and mucous membranes (mouth tissue), swimming pools, household sinks, garbage containers, bathroom appliances, etc.

The amounts of the biocidal composition useful in the method of the present invention may vary widely as long as enough is used that there is produced a sufficient amount of chlorine dioxide in the microenvironment immediately above the surface to be treated. This amount varies with the particular surface to be treated and the kind and degree of contamination. The exact amount may be readily ascertained by routine experimentation.

The present invention is further illustrated by the following Examples. Unless otherwise specified, all weights are in grams, volumes are in milliliters and percentages are by weight in the Examples and throughout this specification.

EXAMPLE 1

This Example illustrates the preparation of a biocidal composition wherein the organic acid-generating agent is encapsulated within a film forming polymer.

The following three solutions are prepared:
  "Solution 1" contains 240 milliliters of 5% by weight poly(vinyl alcohol) (PVA) that is chilled to 3° C.
  "Solution 2" contains 2.56 grams of sodium carbonate and 1.50 grams of 1,6-hexanediamine in 20 milliliters of deionized water.
  "Solution 3" contains 1.00 grams of poly(DL-lactide) (DL-PL), 2.09 grams of sebcoyl chloride, and 1.08 grams of poly[methylene(polyphenyl)isocyanate] dissolved in 20 milliliters of methylene chloride.

Solution 1 is added to a 300-milliliter resin kettle which is submerged in an ice bath. As Solution 1 is stirred at 2000 rpm with a Teflon turbine impeller, Solution 3 is added to the resin kettle. A stable oil-in-water emulsion is formed. Solution 2 is then added to the resin kettle to initiate polymerization at the interface of the oil microdroplets. After 2 hours, the reaction is quenched and the NYLON microcapsules are placed in 1 liter of 25:75 sorbitol: deionized water for 48 hours. The sorbital/water solution extracts the methylene chloride from the microcapsules while allowing water and sorbitol to diffuse into the microcapsules.

Soft, spherical microcapsules are collected by vacuum filtration and placed in to a solution of 40 grams of sodium chlorite in 100 grams of deionized water. This solution is placed in the dark and maintained at 4° C. The NYLON microcapsules are kept in the sodium chlorite for 16 hours to allow sodium chlorite to diffuse into the microcapsules. After equilibrium is reached, the NYLON microcapsules are collected, soaked in a 0.1 N hydrochloric acid solution for 1 hour, and collected by vacuum filtration.

The microcapsules thus formed contain the sodium chlorite and DL-PL encapsulated in a polyamide wall. Because these polyamide microcapsules are somewhat porous, they are coated with a water-insoluble, film-forming polymer (polystyrene) to retain the water and sodium chlorite inside the microcapsules. The microcapsules are coated with polystyrene by suspending them in a solution of methylene chloride and polystyrene. With stirring, a coacervate inducer is pumped into the resin kettle and the polystyrene is coated onto the polyamide microcapsules. When the coacervation is complete, the microcapsules are hardened in 3 liters of stirred heptane and then collected by vacuum filtration.

These microcapsules have continuous polymer films around the polyamide microcapsules. Release of chlorine dioxide from these microcapsules is determined using a potassium iodide/sodium thiosulfate titration. This microcapsule formulation releases chlorine dioxide at a fairly constant rate, averaging 26 μg per day per gram of microcapsule formulation.

EXAMPLE 2

This Example illustrates the preparation of a biocidal composition wherein the organic acid-generating compound is encapsulated by a film forming polymer.
  The following solutions are prepared:

"Solution 1" is an aqueous solution containing 4.0% by weight poly(lactic acid) microspheres (DL-PL), 4.0% by weight sodium chlorite, 1.3% by weight sodium bicarbonate, 5.3% by weight sodium carbonate monohydrate, 35.3% by weight glycerol (humectant), and 1.8% by weight 1,6-hexanediamine.

"Solution 2" contains 0.1% by volume adipoyl chloride in 50:50 sesame oil/cyclohexane.

"Solution 3" contains 2 grams of polystyrene in 100 grams of methylene chloride.

The DL-PL microspheres described in Solution 1 above are prepared by dissolving the DL-PL in methylene chlorine. After dissolution, the polymer solution is added to a stirred aqueous processing medium containing a surfactant. After a stable oil-in-water emulsion is formed (the oil droplets contain the DL-PL and methylene chloride), the pressure inside the reaction vessel is reduced to remove the methylene chloride. When the microspheres are hard, they are isolated by filtration and dried in a vacuum chamber.

One hundred milliliters of Solution 2 is added to a 250 milliliter resin kettle and stirred at about 450 rpm with a 1.5-inch Teflon turbine impeller. Five milliliters of Solution 1 is vortexed for 10 seconds to suspend the DL-PL microspheres. This suspension is then dispersed into Solution 2. Following polymerization (about 10 minutes), stirring is stopped and the NYLON microcapsules are allowed to settle to the bottom of the resin kettle. Solution 2 is decanted and Solution 3 is then added to the resin kettle and stirred at 450 rpm. When the NYLON microcapsules are well suspended, a coacervate inducer is pumped into the resin kettle. The embryonic microcapsules formed are then poured into 3 liters of heptane, stirred in the heptane for 30 minutes, and collected on a fritted-glass funnel.

This process results in hard microcapsules that may be isolated by filtration. Moreoever, when crushed, these hard microcapsules release water, indicating that water is successfully encapsulated. These microcapsules have continuous polymer films but are slightly agglomerated.

EXAMPLE 3

This Example illustrates the effects of polymer molecular weight and copolymer composition on the release of chlorine dioxide from formulations containing sodium chlorite and polymeric acids.

For each formulation, 0.5 grams of sodium chlorite are dissolved in 25 milliliters of deionized water contained in a 125-milliliter Erylenmeyer flask. Next, 0.5 grams of the polymeric acid to be tested are added to each flask. The pH of the resulting solution is then lowered to about 6 with 200 microliters of 1 N acetic acid. Each flask is sealed and covered with tin foil to prevent light-induced decomposition of any chlorine dioxide that is produced.

Periodically, nitrogen is bubbled for 10 minutes through the contents of each sample flask. During this bubbling, each sample flask is connected to a 250-milliliter collection flask containing 125 milliliters of deionized water. The nitrogen from the sample flask (now carrying chlorine dioxide) is bubbled into the 125 milliliters of water in the collection flask to trap the chlorine dioxide for analysis. Potassium iodide is then added to each collection flask and the amount of chlorine dioxide present is determined by titration with a standardized sodium thiosulfate solution.

Figure 2:
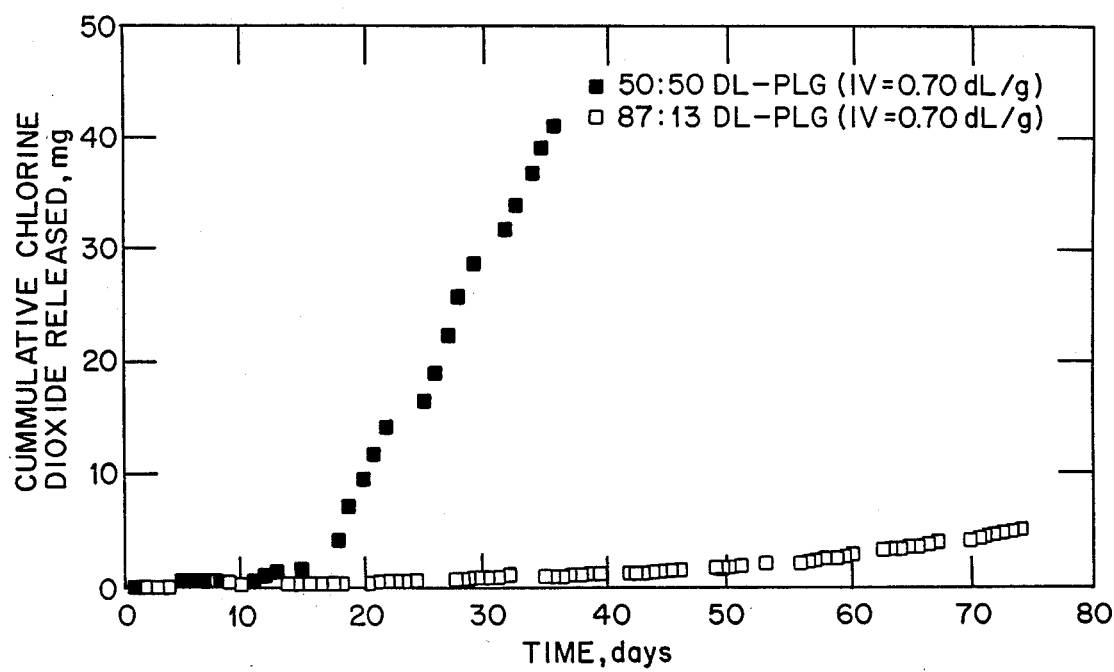
FIG. 2 is a graph showing the release of chlorine dioxide over time from compositions containing sodium chlorite and either 50:50 or 87:13 DL-PLG copolymers.

FIGS. 1 and 2 show the results of several experiments using the above procedure. The release of chlorine dioxide from formulations comprising (a) a low-molecular-weight 50:50 poly(DL-lactide-co-glycolide) (DL-PLG) copolymer which has an inherent viscosity (IV) of about 0.18 dL/g, and (b) a methylvinyl ether/maleic anhydride copolymer are shown in FIG. 1. These formulations release chlorine dioxide at a very fast rate. When DL-PLG copolymers with higher molecular weights (IV of about 0.7 dL/g) are used, the release of chlorine dioxide is much lower as shown in FIG. 2. Moreover, the 50:50 DL-PLG formulation releases chlorine dioxide at a faster rate than does the 87:13 DL-PLG. This faster release with the 50:50 composition probably results from the fact that 50:50 DL-PLG hydrolyzes much faster to produce acid than does 87:13 DL-PLG.

By selecting copolymers with the appropriate molecular weight and lactide-to-glycolide mole ratio, formulations may be prepared that will release chlorine dioxide at the desired level for weeks to years.

The principles, preferred embodiments and modes of operation of the invention have been described in the foregoing specification. The invention which is intended to be protected herein, however, is not to be construed as limited to the particular forms disclosed, since these are to be regarded as illustrative rather than restrictive. Variations and changes may be made by those skilled in this art without departing from the spirit of the invention.

We claim:

1. A long-acting biocidal composition comprising a chlorine dioxide-liberating compound and sufficient hydrolyzable organic acid-generating polymer to lower the pH of said composition to less than about 7, said organic acid-generating polymer being present in a form whereby it is released gradually in the presence of water.

2. The composition of claim 1 wherein the organic acid which is generated in water from said organic acid-generating polymer is at least one member selected from the group consisting of lactic, maleic and glycolic.

3. The composition of claim 2 wherein said organic acid is lactic acid.

4. The composition of claim 1 wherein said composition additionally contains a humectant.

5. A long-acting biocidal composition comprising a chlorine dioxide-liberating compound and sufficient hydrolyzable organic acid-generating polymer to lower the pH of said composition to less than about 7, said organic acid-generating polymer being in the form of discrete microspheres or microparticles which hydrolyze in the presence of water.

6. The composition of claim 5 wherein the organic acid which is generated in water from said organic acid-generating polymer is at least one member selected from the group consisting of lactic, maleic and glycolic.

7. The composition of claim 6 wherein said organic acid is lactic acid.

8. The composition of claim 7 wherein said composition additionally contains a humectant.

9. A long-acting biocidal composition comprising a chlorine dioxide-liberating compound and sufficient hydrolyzable organic acid-generating polymer to lower the pH of said composition to less than about 7, said organic acid-generating polymer being encapsulated by a film forming polymer which will allow sufficient water to contact said organic acid-generating compound to generate said organic acid.

10. The composition of claim 9 wherein the organic acid which is generated in water from said organic acid-generating polymer is at least one member selected from the group consisting of lactic, maleic and glycolic.

11. The composition of claim 10 wherein said organic acid is lactic acid.

12. The composition of claim 11 wherein said composition additionally contains a humectant.

13. The composition of claim 8 wherein said humectant is selected from the group consisting of glycerol and sorbitol.

14. A method of disinfecting a surface over a prolonged period of time comprising applying to said surface a small but biocidally effective amount of a long-acting biocidal composition comprising a chlorine dioxide-liberating compound and sufficient hydrolyzable organic acid-generating polymer to lower the pH of said composition to less than about 7, said organic acid-generating polymer being present in a form whereby it is released gradually in the presence of water.

15. A method of disinfecting a surface over a prolonged period of time comprising applying to said surface a small but biocidally effective amount of a long-acting biocidal composition comprising a chlorine dioxide-liberating compound and sufficient hydrolyzable organic acid-generating polymer to lower the pH of said composition to less than about 7, said organic acid-generating polymer being in the form of discrete microspheres which hydrolyze in the presence of water.

16. A method of disinfecting a surface over a prolonged period of time comprising applying to said surface a small but biocidally effective amount of a long-acting biocidal composition comprising a chlorine dioxide-liberating compound and sufficient organic acid-generating polymer to lower the pH of said composition to less than about 7, said organic acid-generating polymer being encapsulated by a film forming polymer which will allow sufficient water to contact said organic acid-generating compound to generate said organic acid.

* * * * *